(12) United States Patent
Cocozzella et al.

(10) Patent No.: US 8,839,836 B2
(45) Date of Patent: Sep. 23, 2014

(54) DEVICE AND METHOD FOR PRODUCING SANITARY PRODUCTS

(75) Inventors: Nicola Cocozzella, Pescara (IT); Francesco D'Aponte, Pescara (IT)

(73) Assignee: Fameccanica.Data S.p.A., Sambuceto di San Giovanni Teatino (Chieti) (IT)

( * ) Notice: Subject to any disclaimer, the term of this patent is extended or adjusted under 35 U.S.C. 154(b) by 238 days.

(21) Appl. No.: 13/126,881

(22) PCT Filed: Oct. 8, 2009

(86) PCT No.: PCT/IB2009/054418
§ 371 (c)(1),
(2), (4) Date: Apr. 29, 2011

(87) PCT Pub. No.: WO2010/049832
PCT Pub. Date: May 6, 2010

(65) Prior Publication Data
US 2011/0203431 A1    Aug. 25, 2011

(30) Foreign Application Priority Data

Oct. 30, 2008    (IT) .............................. TO2008A0807

(51) Int. Cl.
| B32B 37/00 | (2006.01) |
| B32B 37/02 | (2006.01) |
| B32B 38/00 | (2006.01) |
| B32B 38/04 | (2006.01) |
| B32B 38/18 | (2006.01) |
| B65H 39/14 | (2006.01) |
| B65H 35/08 | (2006.01) |
| B26D 11/00 | (2006.01) |
| A61F 13/15 | (2006.01) |
| B65H 37/04 | (2006.01) |
| B26D 1/62 | (2006.01) |

(52) U.S. Cl.
CPC ................ *A61F 13/15* (2013.01); *B65H 39/14* (2013.01); *B32B 38/04* (2013.01); *B65H 35/08* (2013.01); *B26D 11/00* (2013.01); *B65H 2801/57* (2013.01); *B65H 37/04* (2013.01); *B26D 1/626* (2013.01)
USPC ........... 156/519; 156/250; 156/256; 156/263; 156/265; 156/300; 156/303; 156/510; 156/511; 156/516; 156/517

(58) Field of Classification Search
CPC ... A61F 13/15; A61F 13/15764; B32B 38/04; B32B 2038/045; B65H 37/04; B65H 39/14; B65H 35/08; B26D 1/626; B26D 11/00
USPC ......... 156/250, 256, 263, 265, 300, 303, 510, 156/511, 516, 517, 519
See application file for complete search history.

(56) References Cited

U.S. PATENT DOCUMENTS

| 4,642,150 | A | | 2/1987 | Stemmler |
| 4,786,346 | A | * | 11/1988 | Ales et al. .................... 156/160 |
| 5,407,513 | A | | 4/1995 | Hayden et al. |
| 6,520,236 | B1 | * | 2/2003 | Rajala ............................ 156/511 |
| 2004/0007328 | A1 | | 1/2004 | Popp et al. |

FOREIGN PATENT DOCUMENTS

| EP | 1 132 325 | | 9/2001 |
| EP | 1 864 768 | | 12/2007 |
| JP | 2002-516802 | | 6/2002 |
| JP | 2007-508220 | | 4/2007 |
| JP | 2008-194493 | | 8/2008 |
| WO | WO 99/62801 | | 12/1999 |
| WO | WO 2004/007328 | | 1/2004 |
| WO | WO 2005/035414 | A1 | 4/2005 |

OTHER PUBLICATIONS

International Search Report for PCT/IB2009/054418, mailed Mar. 12, 2010.
Written Opinion for PCT/IB2009/054418, mailed Mar. 12, 2010.
Japanese Patent Office Action dated Jul. 30, 2013, from Japanese Patent Application No. 2011-533857, and its English translation (titled "Summary of 'Notice of Reasons for Rejection'").

* cited by examiner

Primary Examiner — Mark A Osele
Assistant Examiner — Christopher C Caillouet
(74) Attorney, Agent, or Firm — Nixon & Vanderhye P.C.

(57) ABSTRACT

A device for applying at spaced positions ($P_1$, X) over a moving web of material (S) superposed strips of a first (A) and a second (B) includes a first (10, 12) and a second (20, 22) cutting unit arranged cascading with respect to each other. Each unit includes a rotary knife (10, 20) that can be fed with the respective material (A, B) and an anvil roll (12, 22) which cooperates with the respective knife (10, 20) to cut the above-mentioned strips of material (A, B). The anvil rolls (12, 22) of the two units are arranged facing each other, movable of concordant motions with respect to each other and configured in such a manner to transfer the strips of the first material (A) from the first anvil roll (12) over the second anvil roll (22) superimposing them to the strips of the second material (B). The second anvil roll (22) then provides for passing over the moving web of material (S) the strips of the first (A) and second material (B) superimposed to each other.

11 Claims, 3 Drawing Sheets

DEVICE AND METHOD FOR PRODUCING SANITARY PRODUCTS

This application is the U.S. national phase of International Application No. PCT/IB2009/054418 filed 8 Oct. 2009 which designated the U.S. and claims priority to IT Application No. TO2008A000807 filed 30 Oct. 2008, the entire contents of each of which are hereby incorporated by reference.

FIELD OF THE INVENTION

The present disclosure refers to the techniques for producing sanitary products.

DESCRIPTION OF THE RELATED ART

The cutting units of the "Cut & Slip" type have been known and applied over the years on the production lines of sanitary products such as disposable sanitary products.

An example of a Cut & Slip unit is described in Italian patent IT 1183882, which discloses a method for manufacturing a cutting unit capable of applying over a continuous web elements cut at a well defined pitch, determined by the speed of the roller serving as an anvil roll.

The unit described in such patent is distinguished for its essentiality. However, the evolution of products and the increase of the production machine speed have required further development of the unit, like the one described, for example, in documents such as EP-B-0 943 305, EP-B-0 990 588 or EP-A-1 864 768.

The solutions described in these documents overcome various drawbacks regarding the cutting units which require the slipping of the element to be cut to move it at the application pitch.

In particular, the solution described in EP-B-0 943 305 provides for making a unit for cutting laminated elements eliminating the problem of format change, a problem overcome in the conventional unit though complete replacement of the unit itself.

The solution described in EP-B-0 990 588 provides for obtaining a system for managing sub-atmospheric pressure ("vacuum") for dragging and holding the element cut by the head.

The solution described in EP-A-1 864 768 provides for obtaining a unit that overcomes both the format change and vacuum management drawbacks.

Figure 1:
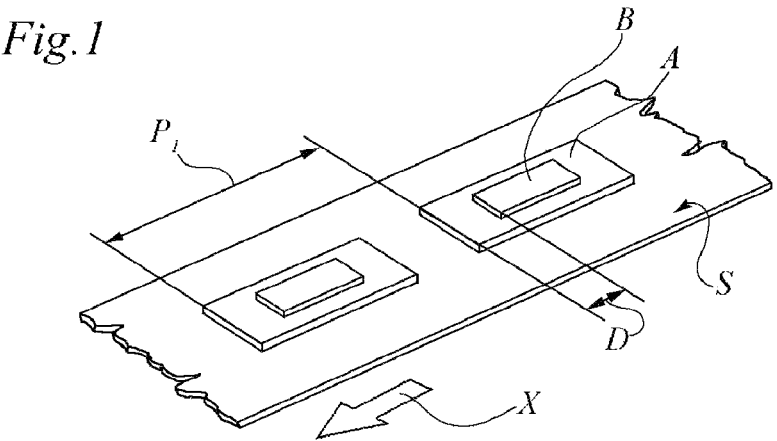

When manufacturing sanitary products there arises the need to provide products or component products with multiple elements in form of strips applied over each other, for example as illustrated in FIG. 1. Represented herein is a web of support material S which advances in a given direction, identified in the figures by the arrow X, on which strips or stubs of material A are stuck at a pitch (i.e. at predefined distances), in turn applied on such strips or stubs being strips or stubs of material B.

Figure 2:
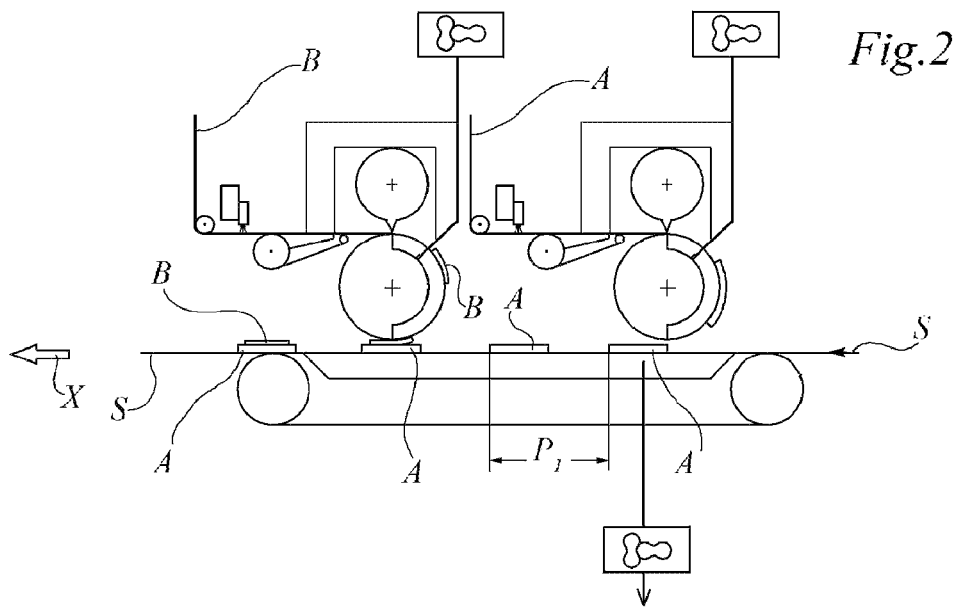

FIG. 2 represents a possible layout of a system useable to obtain the elements illustrated in FIG. 1. In practice, these are two Cut & Slip units following each other in a cascading manner: the first unit receives material S and applies material A thereon; then the second unit applies the elements of material B on the elements of material A. In this case it is assumed that, as it usually occurs, materials S, A and B are in form of webs.

Applying an element of material A on a support S with a "pitch" $P_1$ (see FIG. 1) inevitably implies positioning errors regarding element A due to the elasticity of the material S and due to technological imperfections of the various components and transmission.

In addition to the abovementioned positioning errors there also arises analogous errors linked to the application of material B on material A. In particular, the positioning regarding materials A and B, identified by the dimension D in FIG. 1, is negatively influenced by the error related to the pitch $P_1$ for the application of the elements of material A onto the base material S.

Figure 3:
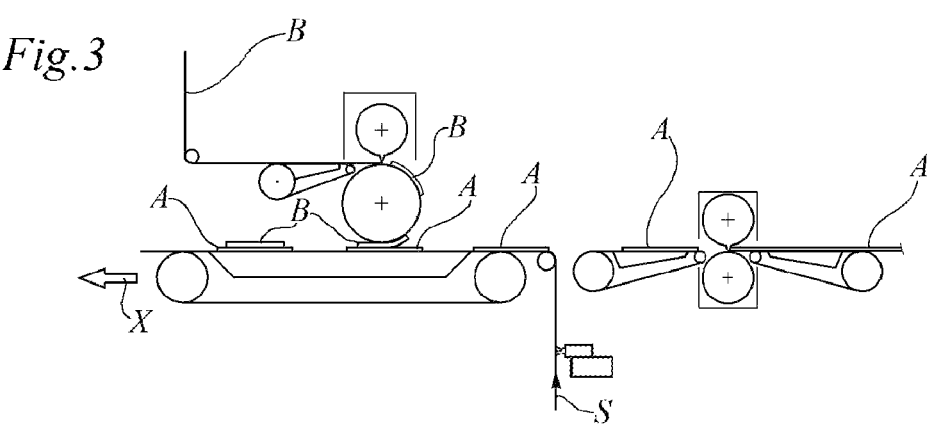
Figure 4:
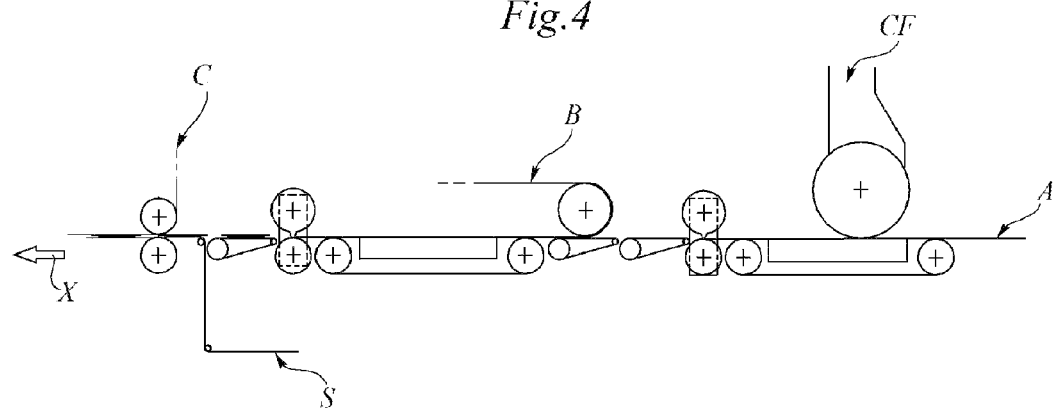

This also occurs in cases where—as illustrated in FIGS. 3 and 4—one of the two cascade units is a Cut & Slip unit of a non-conventional type, i.e. of the "pitchless" type as described in EP-B-0 943 305.

In particular, FIG. 4 illustrates a solution wherein material A is cut first (after applying a cellulose fibre material), a first spacing is carried out, material B is coupled to material A, material B is cut and the second spacing is carried out.

The inventors observed that the abovementioned drawbacks are getting more and more serious and common. This due to the fact that sanitary products such as absorbent products are becoming thinner and thinner. In addition, there is an ever-growing trend of replacing absorbent material made of fibres (fluff) with superabsorbent material (for example hydrogelling absorbent materials such as the SuperAbsorbing Polymer or SAP). This leads to quite delicate absorbent cores, not rigid at all, hence implying the manipulation difficulty derived therefrom.

In particular, a process like the one illustrated in FIG. 4 becomes quite critical to manage, especially in the region of the second spacing, in cases where material B is actually a ultra thin absorbent core, with extremely high SAP percentages, i.e. beyond 60% of the total weight of the core.

OBJECT AND SUMMARY OF THE INVENTION

In the general framework outlined above there arises the need of providing solutions capable of overcoming the drawbacks outlined previously.

The present invention has the object of providing such solution.

According to the present invention, such object is attained due to a device having the characteristics specifically referred to in the claims that follow. The invention also regards a corresponding method.

The claims form an integral part of the technical disclosure provided herein in relation to the invention.

BRIEF DESCRIPTION OF THE ATTACHED REPRESENTATIONS

Now, the invention shall be described, purely for exemplary and non-limiting purposes, with reference to the attached representations, wherein:

FIGS. 1 to 4 have already been described previously, and

Figure 5:
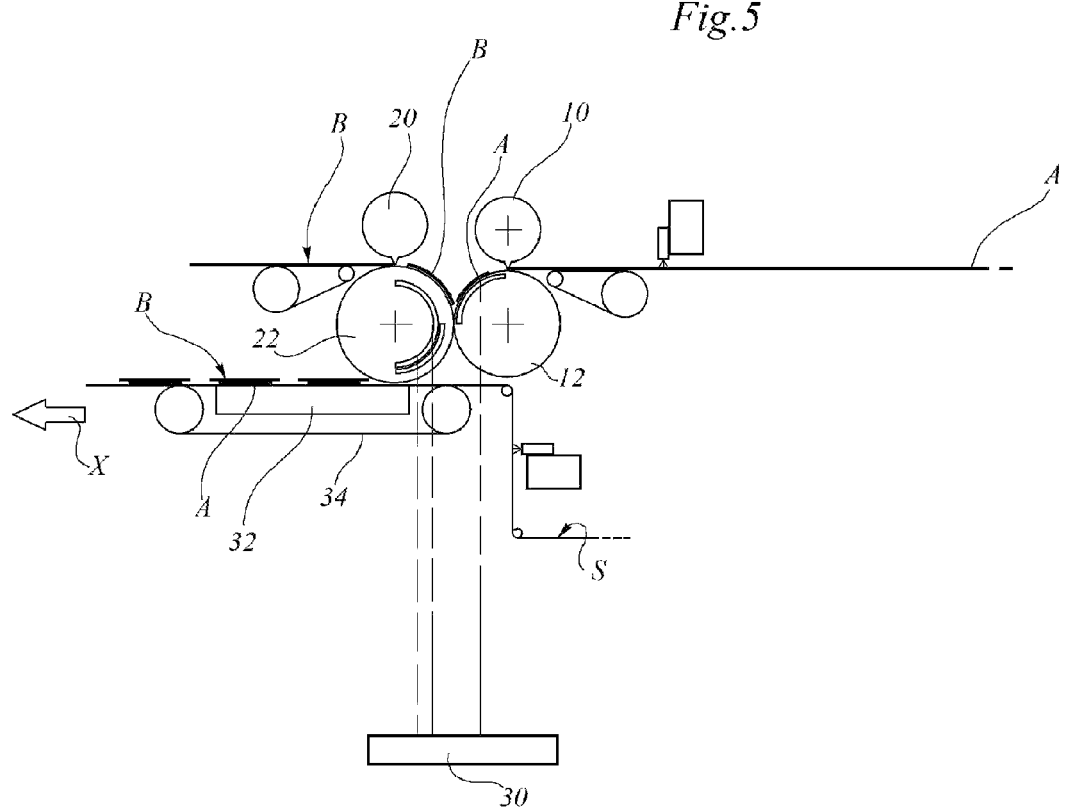
Figure 6:
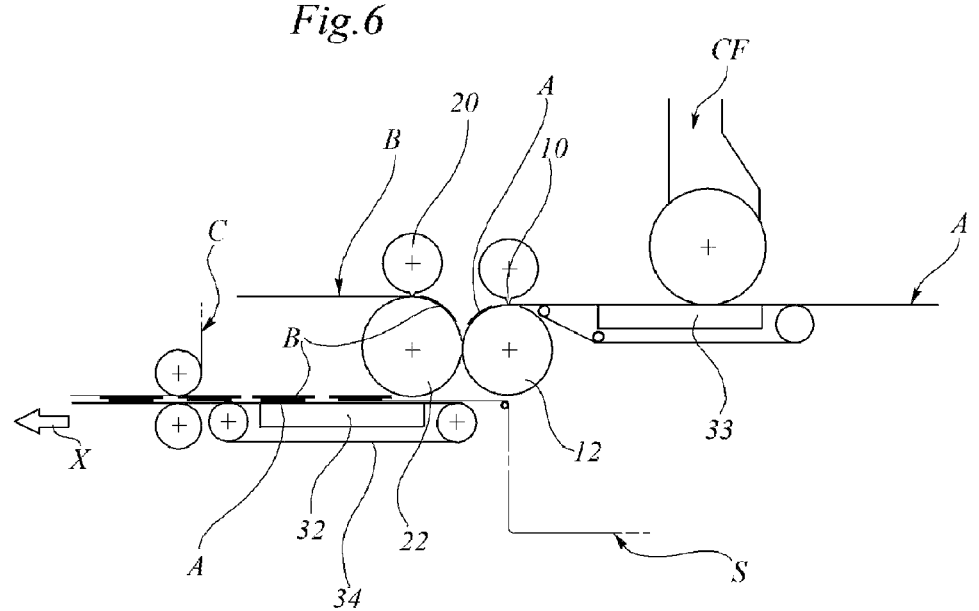

FIGS. 5 and 6 illustrate two possible embodiments of the solution described herein.

DETAILED DESCRIPTION OF THE EMBODIMENTS

Illustrated in the following description are various specific details aimed at an in-depth understanding of the embodiments. The embodiments may be obtained without one or more specific details, or through other methods, components, materials etc. In other cases, known structures, materials or operations are not shown or described in detail to avoid obscuring the various aspects of the embodiments.

Reference to "an embodiment" in this description indicates that a particular configuration, structure or characteristic described regarding the embodiment is included in at least one embodiment. Hence, expressions such as "in an embodiment", possibly present in various parts of this description do not necessarily refer to the same embodiment. Furthermore, particular configurations, structures or characteristics may be combined in any suitable manner in one or more embodiments.

References herein are used for facilitating the reader and thus they do not define the scope of protection or the range of the embodiments.

FIG. 5 illustrates a first embodiment which allows obtaining a structure like the one illustrated in FIG. 1.

To fix the ideas (obviously without this being considered restrictive with respect to the scope of the invention in any way whatsoever) it can be assumed that materials S, A and B are, for example, respectively:

the so-called backsheet of an absorbent sanitary product such as for example a children's diaper, a so-called "patch" or "acquisition or diffusion layer" applied on the absorbent core; and the absorbent core (for example of the ultra thin type, with extremely high percentages of SAP—Superabsorbent Polymers—beyond 60% of the total weight of the core) applied on the backsheet.

The characteristics of such materials are to be deemed per se known and thus such not to require a detailed description herein.

In this example, it is assumed that materials S, A and B be initially in form of webs that are unwound from respective supply sources (reels). Obviously, the information provided above shall not be deemed restrictive in any manner whatsoever: one or more of the considered materials could also be produced directly from the production line or be provided in different form with respect to the classic rolls form.

References 10 and 12, on one hand, and references 20 and 22, on the other hand, respectively indicate the rotary knife and the corresponding element serving as an anvil roll of a first and a second Cut & Slip unit intended to segment the webs of the materials A and B into strips and apply them "at pitch" on the web S.

Except for the information provided hereinafter, the two units 10, 12 and 20, 22 may be devices of the known type, for example corresponding to the disclosures provided in the documents mentioned in the introductive part of the present description.

For example, this might be the case, with reference to FIG. 5, of units wherein the treated materials are maintained at contact (with capacity to slip) with the anvil rolls 12 and 22 due to the sub-atmospheric pressure ("vacuum") generated by a source such as a suction pump 30.

A sub-atmospheric pressure level generated by the source 30 may also be sent towards a vacuum box 32 associated to a movement structure (i.e. a conveyor, such as for example a motor-driven belt or roller 34) which moves the web of material S applied over which, superimposed to each other, are elements or strips of materials A and B. The sub-atmospheric pressure present in the box 32 is intended to maintain the strips of materials A and B at contact with material S.

The fixing of the strips of materials A and B to each other and/or onto material S may be obtained through different criteria (for example through adhesive means, due to the sandwich entrapment between the backsheet S and a topsheet applied above the strips A and B, through thermomechanical or ultrasonic welding, etc.), not essential for the understanding of the solution outlined herein.

The solution illustrated in FIG. 5 tackles the problem of eliminating the positioning errors regarding strips of material A and B applying the patch of material A over the strip of material B directly on the anvil roll 22 of the unit 20, 22 which treats material B itself: in the embodiment illustrated herein it is the case of the unit 20, 22 located downstream with reference to the advancement direction of the material A.

In an embodiment, the units 10, 12 and 20, 22 may be of the type described in document EP-A-1 864 768, i.e. the cutting unit of the "pitchless" type, in that not provided with format change.

In the illustrated embodiment, the two anvil rolls 12, 22 and the main web (that corresponding to material S) may all move at the same speed, with the possibility of providing the "format change" function entirely by means of a software.

The management of the sub-atmospheric pressure levels present in the anvil rolls 12 and 22 (and of the box 32) is carried out, according to per se known criteria, depending on the type and size of the treated materials, as well as on the position regarding the trips.

In an embodiment, a vacuum level capable of seizing and moving both elements A and B to coupling with the web S shall be applied to the unit which treats the material B, onto which the patch of material A is applied.

Thus, the solution described herein allows accurately applying—in spaced position ($P_1$, D of FIG. 1) over a moving web of material S—strips of a first and a second material (A and B) superimposed to each other.

As a matter of fact, applying the first element onto the second one when the latter (already cut or to be cut) is still on the anvil roll 22 leads to obtaining the coupling between the two strips in question operating on a rigid structural element. This allows avoiding inaccuracies linked to the traditional method of operating wherein the application operation actually occurs on the web S and, obviously, in various positions on the processing line, i.e. in conditions wherein the elasticity of the material S may be a source of poor positioning accuracy ($P_1$+D).

In the illustrated embodiment, the device includes two Cut & Slip units 10, 12 and 20, 22, each including a first knife 10, 20 to be fed with the respective material A or B and an anvil roll 12, 22 suitable to cooperate with the corresponding knife 10, 20 to cut the strips intended to be applied superimposed to each other at a spaced position over a moving web of material S (arrow X of FIG. 1).

The spacing function is allowed by the fact that the strips can slip on the anvil rolls 12 and 22, thus varying the distance that separates them (initially zero at the cutting step).

The anvil rolls 12 and 22 (in form of two rollers herein, but they also could be represented by any other type of rotary bodies) are arranged facing each other and are movable of concordant motions with respect to each other (i.e. oriented to the same direction) at the (almost) tangency point and transfer of the strip A over the material B. In the embodiment illustrated herein they are represented by counter-rotating rollers facing each other, i.e. rollers arranged with their axes parallel to each other and, as mentioned, in almost tangency conditions with respect to each other, where anvil roll 22 rotates clockwise, while anvil roll 12 rotates anticlockwise. Thus, the first anvil roll 12 is capable of passing the strips of the first material A over the second anvil roll 22 superimposing them to the strips of the second material B borne by the second anvil roll (22)—always with relative slip capacity (i.e. with the possibility to vary the distance separating them).

For such purpose, the second anvil roll 22 is provided with retention means (source of vacuum 30) adjustable in such a manner that the anvil roll 22 is not only capable of withholding the strips of the second material B but also drawing to itself the strips of the first material A cut by the first unit 10, 12 allowing the strips A and B to be superimposed to each other.

The second anvil roll 22 is thus capable of dragging the strips A and B superimposed to each other. Furthermore, being arranged facing each other at the proximal end of the belt conveyor 34, the second anvil roll 22 is then capable of passing the strips A and B superimposed to each other over the belt conveyor 34 itself.

The process schematised in FIG. 5 may also be obtained in the embodiment of FIG. 6 where the possible application over the material A made of cellulose fibre CF is provided for with the possible presence of a respective associated vacuum box 33.

Alongside the technological advantage of obtaining a higher quality product, the positioning tolerances between the various narrower elements (i.e. minimisation of the errors on positioning parameters $P_1$ and D—see FIG. 1) allows obtaining another advantage given by the fact that the process of assembling the elements A, B and S is more compact, and thus much less costly.

The solution described herein (if compared with the traditional solutions indicated in FIGS. 2-4) in particular allows eliminating three belt conveyors, the system for coupling material B with material A and the respective motor-driving means. Furthermore, being more compact the processing line considerably reduces the cost of the framework and accessories connected thereto such as protective casings (front and rear) electrical channels etc.

A particular case of application may be obtained in embodiments wherein the first cutting unit 10, 12 is not (at least as implicitly assumed up to this point) a Cut & Slip unit, but a Cut & Lay unit, i.e. a unit that cuts, but does not space the strips of material deriving from the cutting operation.

This case may also occur when the material, usually material A, is a particularly fragile core and on which a shaped cut is carried out.

In this case, when the knife 10 cuts the material A, all the elements involved in this operation, i.e. the knife 10, anvil roll 12 and web A, move at the same speed.

As mentioned beforehand, the cut may be straight or shaped. In the latter case, possible wastage materials are removed through known techniques and means not indicated in the drawing.

After cutting, the strip or stub of material A is transferred onto material B, when the latter is still positioned on the anvil roll 22 and the respective strip of material B has not yet been cut by the corresponding knife 20.

After completing the transfer, the knife 20 cuts material B and the element made up of the two coupled strips of material A and B is spaced by the anvil roll 22 and applied over the web S.

Without prejudice to the principle of the invention, the details and embodiments may vary, even significantly, with respect to what has been described herein by way of non-limiting example only, without departing from the scope of the invention as defined by the attached claims.

The invention claimed is:

1. A device for applying at spaced positions ($P_1$, D) over a moving web of material (S) superposed strips of a first material (A) and a second material (B), the device comprising:
   a first cutting unit including a first knife to be fed with said first material (A) and a first anvil roll to co-operate with said first knife in cutting said strips of said first material;
   a second cutting unit including a second knife to be fed with said second material (B) and a second anvil roll to co-operate with said second knife in cutting said strips of said second material to be applied superposed with strips of said first material (A) at spaced positions ($P_1$, D) over said moving web of material (S),
   wherein said first anvil roll and said second anvil roll are arranged facing each other, movable of concordant motions relative to one another, and configured for passing said strips of said first material (A) onto said second anvil roll by superposing them onto said strips of said second material (B) carried with a capability of sliding by said second anvil roll such that the strips of the first material (A) and the strips of the second material (B) can slip on the first and second anvil rolls, thus varying a distance, at a cutting step, between the strips of the first material (A) and the strips of the second material (B).

2. The device of claim 1, wherein said first and second cutting units are configured to allow sliding of said strips.

3. The device of claim 1, wherein at least one of said cutting units does not allow sliding of said strips.

4. The device of claim 3, wherein said at least one of said cutting units includes a patterned knife.

5. The device of claim 1, further including a conveyor for said moving web of material (S), said conveyor configured for receiving from said second anvil roll said strips of said first material (A) and said strips of said second material (B) superposed to each other.

6. The device of claim 5, wherein said conveyor includes at least one of a motorized belt and a motorized roller.

7. The device of claim 5, wherein said conveyor is provided with vacuum retain means to retain said moving web of material (S) having applied thereon said strips of said first material (A) and said strips of said second material (B) superposed to each other.

8. The device of claim 1, wherein said second anvil roll is provided with capture means to retain said strips of said first material (A) superposed to said strips of said second material (B) carried with the capability of sliding by said second anvil roll.

9. The device of claim 1, wherein said first anvil roll and said second anvil roll are counter-rotating rollers arranged side-by-side.

10. The device of claim 1, wherein said first anvil roll and said second anvil roll are provided with vacuum retain means to retain said strips with the capability of sliding thereon.

11. The device of claim 1, wherein said first knife and said second knife are rotary knives.

\* \* \* \* \*